United States Patent
Perner et al.

(10) Patent No.: US 10,605,798 B2
(45) Date of Patent: Mar. 31, 2020

(54) METHOD AND DEVICE FOR OPTICAL YARN QUALITY MONITORING

(71) Applicants: Petr Perner, Český Dub (CZ); Ondřej Zelinka, Český Dub (CZ); Josef Suska, Šimonovice (CZ)

(72) Inventors: Petr Perner, Český Dub (CZ); Ondřej Zelinka, Český Dub (CZ); Josef Suska, Šimonovice (CZ)

(*) Notice: Subject to any disclaimer, the term of this patent is extended or adjusted under 35 U.S.C. 154(b) by 62 days.

(21) Appl. No.: 15/854,018

(22) Filed: Dec. 26, 2017

(65) Prior Publication Data

US 2019/0195854 A1    Jun. 27, 2019

(51) Int. Cl.
*G01N 33/36* (2006.01)
*G06T 7/00* (2017.01)
*G01N 21/952* (2006.01)
*G01N 21/88* (2006.01)
(Continued)

(52) U.S. Cl.
CPC ....... *G01N 33/365* (2013.01); *G01N 21/8806* (2013.01); *G01N 21/8851* (2013.01); *G01N 21/952* (2013.01); *G02B 27/4205* (2013.01); *G06T 7/0004* (2013.01); *G06T 7/90* (2017.01); G01N 2021/8835 (2013.01); G01N 2021/8845 (2013.01); G01N 2021/8887 (2013.01); G01N 2201/0634 (2013.01)

(58) Field of Classification Search
CPC ............. G01N 33/365; G01N 21/8806; G01N 21/8851; G01N 2021/8845; G01N 2201/0634; G01N 21/952; G01N 21/8915; G06T 7/0004; G06T 2207/10048; G06T 2207/30108; G06T 2207/30124; G06T 2210/16; G06T 7/62; G02B 27/4205
See application file for complete search history.

(56) References Cited

U.S. PATENT DOCUMENTS

| | | | | |
|---|---|---|---|---|
| 3,709,610 A | * | 1/1973 | Kruegle | B65H 63/065 356/635 |
| 4,887,155 A | * | 12/1989 | Massen | D01G 31/006 348/88 |
| 5,264,909 A | | 11/1993 | Rochester | |

(Continued)

FOREIGN PATENT DOCUMENTS

| CH | 643060 | 5/1984 |
|---|---|---|
| CH | 706948 | 3/2014 |

(Continued)

OTHER PUBLICATIONS

Teikari et al., "Optical Performance: Characterization of a Pupillometric Camera" (Year: 2008).*

(Continued)

*Primary Examiner* — Kenny A Cese
(74) *Attorney, Agent, or Firm* — Stevens & Showalter LLP (57) ABSTRACT

The invention relates to a method and apparatus for monitoring yarn quality in the textile industry. Textile yarn is checked for quality to meet the required criteria such as diameter evenness and unwanted foreign fiber presence. The invention utilizes an artificial light illuminating the yarn, focusing element, diffraction element and the image sensor for capturing of focused diffracted rays from illuminated yarn image. The presence of foreign fibres in yarn and yarn diameter is determined by processing of captured image.

8 Claims, 5 Drawing Sheets

(51) Int. Cl.
*G02B 27/42* (2006.01)
*G06T 7/90* (2017.01)

(56) References Cited

U.S. PATENT DOCUMENTS

| | | | |
|---|---|---|---|
| 5,414,520 | A | 5/1995 | Zellweger |
| 6,242,755 | B1 | 6/2001 | Henze et al. |
| 7,324,201 | B2 | 1/2008 | Birlem |
| 7,333,202 | B2 * | 2/2008 | Birlem ............... G01N 21/8915 356/429 |
| 8,921,473 | B1 * | 12/2014 | Hyman .................... C08K 3/04 423/445 R |
| 2005/0051466 | A1 * | 3/2005 | Carter ..................... B04B 13/00 210/94 |
| 2006/0164646 | A1 | 7/2006 | Ott |
| 2016/0224860 | A1 * | 8/2016 | Koven ................. G06K 9/4652 |
| 2016/0254638 | A1 * | 9/2016 | Chen .................... H04N 13/254 362/11 |
| 2019/0195853 | A1 | 6/2019 | Perner et al. |

FOREIGN PATENT DOCUMENTS

| | | |
|---|---|---|
| CZ | 286113 | 1/2000 |
| CZ | 20014561 | 8/2003 |
| CZ | 298929 | 3/2008 |
| CZ | 299647 | 10/2008 |
| CZ | 20090634 | 4/2011 |
| DE | 19818069 | 10/1999 |
| EP | 1143236 | 10/2001 |
| EP | 1643246 | 4/2006 |
| EP | 1873105 | 1/2008 |
| WO | 2007025350 | 3/2007 |
| WO | 2011147384 | 12/2011 |
| WO | 2012051730 | 4/2012 |

OTHER PUBLICATIONS

Jiri Sloupensky and Rieter CZ s.r.o "Novel Sensors in Rieter CZ: Yarn Sensors for Spinning Machines" Jun. 22, 2015.
Fred H. Hu; Office Action; U.S. Appl. No. 15/854,014; dated Nov. 29, 2019; United States Patent and Trademark Office; Alexandria, VA.

* cited by examiner

METHOD AND DEVICE FOR OPTICAL YARN QUALITY MONITORING

RELATED APPLICATION

This application is related to commonly owned U.S. patent application Ser. No. 15/854,014, entitled: METHOD AND SYSTEM FOR YARN QUALITY MONITORING, filed on Dec. 26, 2017.

FIELD OF THE INVENTION

The invention relates to a method and device for color inspection and diameter measuring of a linear textile formation such as yarn, thread, textile fibers and slivers.

BACKGROUND OF THE INVENTION

Yarn is a textile formation made by spinning of a relatively short fibrous material into a long continuous unit. Raw cotton is used as one of the many input materials for yarn production. Machine yarns are wound onto coils for easy storage and further processing.

Yarn evenness and foreign fibers are important quality parameters in yarn. Yarn evenness refers to the variation in diameter along its length, as yarn has small changes in diameter along its length. There are numerous locations of thick and thin portions along the yarn length. This affects evenness of the yarn. Foreign fiber is the presence of foreign particles in the textile yarn. Textile yarn is generally white in color. Foreign fibers interfere with color homogeneity of the yarn. Yarn color analysis determines the presence of foreign fibers. Yarn evenness and foreign fibers are affected by quality of the materials used. Yarn evenness is also affected during manufacturing by spinning machines. As yarn is produced rapidly and in high volumes, manual inspection by human inspectors is not feasible, but rather, is impractical, and not possible.

SUMMARY OF THE INVENTION

The present invention provides methods and apparatus for monitoring yarn quality for detecting foreign fibres and measuring yarn diameter. The present invention is particularly suitable for mass machine production of yarn, which has increased resistance against accumulated dust particles and which is easily realizable.

Embodiments of the invention are directed to methods of yarn quality monitoring by a primary artificial light source illuminating longitudinally moving yarn. The longitudinally moving yarn is guided by guiding elements, and is split into small consecutively measured yarn segments whose longitudinal dimension is defined by a longitudinal dimension of a photosensitive area of the image sensor, the speed of yarn movement, and the image sensor sampling rate. Image sensor data for each measured yarn segment is used for yarn quality evaluation. The illuminated yarn is placed in front of the image sensor. Light rays, which are reflected from the yarn, are focused on the image sensor and diffracted by diffraction element. The diffracted light creates interference pattern on the image sensor, which is used for color analysis and ultimately foreign fiber detection.

Embodiments of the invention are such that when using a diffraction element, a color image sensor is not necessary, and a monochromatic image sensor may be used. Measured yarn segment color information is obtained by the processing of light intensity at corresponding pixel positions on the image sensor. Corresponding pixel position depends on color wavelength, yarn diameter and yarn position. The monochromatic image sensor has high sensitivity, high resolution, while being inexpensive to use.

Embodiments of the invention utilize a focusing element, which renders the device highly immune to dust particles, which accumulate on both optical surfaces (emitter and receiver). The focusing element also serves to direct unwanted ambient light rays coming from the sides of the yarn away from the image sensor.

Embodiments of the invention also employ a diffraction element with a zero order mode feature, such that a portion of the light rays pass undiffracted through the diffraction element and are focused on the image sensor as a yarn image. The interference pattern created by diffracted rays is captured simultaneously with an image of the yarn by the image sensor, and processed for obtaining color analysis and yarn diameter. For yarn quality monitoring, it is necessary to process color analysis and yarn diameter from the same yarn segment. This is in contrast to the contemporary art, where the yarn segment data for color analysis and the yarn segment data for yarn diameter calculations are captured by separate independent light detectors, requiring data synchronization depending on the speed of the moving yarn.

In embodiments of the invention, two types of light sources are used: a primary light source, whose rays are reflected from the yarn before they reach the image sensor, and, a secondary light source, which directly illuminates an image sensor.

In another embodiment of the invention, a secondary light source (e.g., a secondary artificial light source) is added to the setup with primary light source. Secondary light source directly illuminates the image sensor through a focusing element. The measured yarn is placed between the secondary artificial light source and the image sensor, and the yarn creates an obstacle for the image sensor illumination. The use of a second artificial diffuse light source in combination with the focusing element creates sharp yarn contours images regardless of measured yarn color. Processing of the yarn contour image determines the yarn diameter and processing of the interference pattern determines presence of foreign fibers in the yarn. An advantage of using direct image sensor illumination is that significantly lower power of the secondary artificial light source is needed for exciting image sensor pixels, than that for configurations where reflected light rays are captured on the image sensor for yarn diameter processing.

In embodiments of the invention, diffraction elements are used for diffracting at least a portion of the light rays. Diffracted light rays create an interference pattern on the image sensor. Undiffracted light rays, originating from the primary light source and reflected from the moving yarn, create a yarn image on the image sensor. Undifracted light rays, originating from the secondary light source, directly illuminating the image sensor, create a yarn contour image on the image sensor (the "yarn contour image" or "contour image" is created from yarn shadows and nonblocked secondary light source rays). Image sensor captured data is created as any combination of yarn contour images, yarn images, and interference patterns.

Embodiments of the invention employ monochromatic light, Red-Green-Blue (RGB) light, white light, Ultraviolet (UV) light, and, Infra-Red (IR) light is used as primary artificial light source. This primary artificial light source illuminates the yarn and the image sensor captures light rays reflected from the yarn. Specific light wavelengths or combinations thereof are suitable for foreign fiber detection and monitoring of various yarn materials, e.g. cotton, wool, or synthetic material, such as polypropylene.

Embodiments of the invention use primary artificial light with wavelengths different from secondary artificial light. Such wavelength selection in combination with the optical filter partially covering the image sensor, allows for the use secondary artificial light rays to measure yarn diameter.

Embodiments of the invention are such that parameters of the primary artificial light source and/or the secondary artificial light source are controlled via feedback. This feedback is based on the quality of previously captured images. For example, light intensity is increased when images with low light intensity were previously captured.

Embodiments of the invention are directed to a device for yarn quality monitoring, which includes at least one primary artificial light source illuminating the yarn, at least one focusing element, a diffraction element, image sensor and control unit or controller for processing data from the image sensor (image sensor data).

Embodiments of the invention are such that the diffraction element is a diffraction grating. The advantage of the diffraction grating is simplicity and economics.

Embodiments of the invention are such that the system and device employ monochromatic light, Red-Green-Blue (RGB) light, white light, Ultra Violet (UV) light, Infra-Red (IR) light used as the primary artificial light source. The primary artificial light source illuminates the yarn and the image sensor captures light rays reflected from the yarn. Specific light wavelengths or combinations thereof are suitable for detection and monitoring of various yarn materials, e.g. cotton, wool, or synthetic material, such as polypropylene.

In other embodiments of the device, a secondary artificial light source illuminates the image sensor directly through a focusing element and a diffraction element, which is added.

Other embodiments of the invention utilize a primary artificial light source with wavelengths different from the secondary artificial light source. Such wavelength selection in combination with optical filter, covering partially the image sensor, allows for the use of the primary artificial light source only as a single source for measuring the diameter of the yarn.

In another embodiment of the invention, the device includes sources of primary and/or secondary artificial light, which are controlled via feedback, based on the quality of previously captured images. For example, light intensity is increased when images with low light intensity were previously captured.

In other embodiments of the device according to the invention, the focusing element is formed by at least one lens or a combination of lenses, from the group of aspherical lens, mirror lens, convex lens, and concave lens. Lenses or combinations of lenses can be mounted in an M12×0.5 package. The size and pitch of the M12×0.5 package allows for the adjustment of a focus distance, and the M12×0.5 package is available at low costs.

In other embodiments of the device according to the invention, the image sensor is formed by at least one line or array of light-sensitive pixels. Individual pixels or regions of pixels can be covered with an optical filter layer for specific ranges of light wavelengths. This simplifies further processing of the captured images for diameter measurements and yarn color analysis.

In other embodiments of the device according to the invention, the image sensor pixels can include micro lenses for increased sensitivity and limiting of wide angle light rays, such that the image is made sharper.

In another embodiment of the device according to the invention, the image sensor is a charge coupled device (CCD) type. CCD image sensors are used, as they have high sensitivity and are low cost.

In another embodiment of the device according to the invention, the image sensor is a complementary metal oxide semiconductor (CMOS) type. CMOS image sensors have high speed and low power consumption.

In another embodiment of the device according to the invention, the control unit is provided with a field-programmable gate array (FPGA) or a programmable logic device (PLD) programmable logical array (PLA), or an application specific integrated circuit (ASIC) integrated circuit, for fast parallel image data processing, a microcontroller for yarn quality monitoring, light source control circuits, and a power supply.

In another embodiment of the device according to the invention, an ASIC can be used to integrate image sensor with data processing on one chip.

The present invention is advancement over the contemporary art, as it allows for accurate yarn measurements and color analysis when significant amounts of dust particles are present. Additionally, the invention provides methods and devices able to measure yarn diameters and detect foreign fibres from the same image, as captured by an image sensor.

The advantage of the invention is high reliability even in very dusty environments. In the contemporary art, dust particles have a major effect on the image quality and thus, on the accuracy of yarn diameter measuring and color analysis. The invention provides methods and devices able to measure yarn diameter and detect foreign fibres from the same image, which is captured by an image sensor. Another advantage of the invention is the low cost of the device, which integrates standard low cost components.

Embodiments of the invention are directed to a yarn quality monitoring device or system. The device or system comprises: a primary light source (e.g., a primary artificial light source) for illuminating the yarn; an image sensor illuminated by light from primary light source light reflected from the yarn and propagating along an optical path to the image sensor, the image sensor for capturing an image data; a focusing element in the optical path between yarn and image sensor, for focusing the reflected light on the image sensor; a diffraction element in the optical path between yarn and image sensor, for diffraction of primary light source light reflected from the yarn; and, a controller for processing the image data to obtain color analysis of yarn and yarn diameter.

Optionally, the diffraction element is a diffraction grating.

Optionally, the device or system additionally comprises: a secondary light source (e.g., a secondary artificial light source) emitting light, the light propagation defining an optical path; and, a diffuser proximate to the secondary light source for diffusing the emitted light, diffused light illuminates image sensor over optical path through focusing element and diffraction element, yarn placed as an obstacle in the optical path create yarn contour image on the image sensor used by the controller for yarn diameter processing.

Optionally, the primary light source and the secondary light source emit light at different wavelengths, and the device further includes an optical filter at least partially covering the image sensor for blocking light reflected from the yarn illuminated by the primary light source.

Optionally, the primary light source emits one or more light types including monochromatic light, RGB (Red-Green-Blue) light, white light, UV (ultraviolet light) or IR (infra red) light.

Optionally, the focusing element includes one or more lenses selected from the group consisting of aspherical lenses, mirror lenses, convex lenses, concave lenses and combinations thereof.

Optionally, the focusing element includes one or more lenses in an M12×0.5 package.

Optionally, the image sensor comprises: one or more lines of photosensitive pixels; and, optionally, the image sensor is type of a CMOS (complementary metal oxide semiconductor) sensor or a CCD (charge coupled device).

Optionally, the image sensor includes microlenses configured to limit wide angle light rays.

Optionally, the controller comprises: a programmable logic array (PLA) for image data processing, to obtain yarn diameter and/or yarn color analysis; a light control circuit in communication with the PLA, which is controlled by the PLA; and, a microcontroller in communication with the PLA, the microcontroller programmed to evaluate the yarn eveness, and/or the yarn foreign fiber content, from the processed image data.

Embodiments of the invention are directed to a method of yarn quality monitoring. The method comprises: illuminating a moving yarn by a primary light source configured for creating an interference pattern on an image sensor, the primary light source light reflected from the yarn and diffracted by a diffraction element and focused by focussing element on the image sensor, the diffraction element and focusing element aligned to define an optical path along which the primary light source light propagated when reflected off moving yarn; obtaining an interference pattern by the image sensor; and, processing the interference pattern to obtain color analysis of the yarn.

Optionally, the method further comprises: passing of part of light reflected from the yarn through the diffraction element undiffracted; capturing the focused undiffracted light by the image sensor as yarn image; and, processing the yarn image to determine at least one diameter of the yarn.

Optionally, the method further comprises: illuminating the image sensor with light from secondary light source configured for creating a contour image of the moving yarn on the image sensor, the secondary light source light diffused by the diffuser and focused by the focusing element, on the image sensor, the secondary light source, diffuser and focusing element in an alignment to define an optical path; obtaining a contour image of the yarn by the image sensor, the moving yarn positioned in the optical path between the primary light source and the image sensor; and, processing the yarn contour image to obtain a yarn diameter.

Optionally, the primary light source emits at least one type of light including: monochromatic light, RGB light, white light, UV light, IR light, and combinations thereof.

Optionally, the illuminating by the primary light source is at a wavelength different from a wavelength of light emitted from the secondary light source, and further comprising: covering a portion of the image sensor with an optical filter; passing the emitted light from the secondary light source through the optical filter to a portion of the image sensor; and, blocking light reflected from the yarn, to cause illumination from only the secondary light source for measuring a diameter of the moving yarn.

Optionally, the capturing of the contour image of the moving yarn and the capturing of the interference pattern is performed simultaneously by the image sensor.

Optionally, the method additionally comprises: controlling the primary light source to emit light at an intensity based on processing results from a previously captured image from the image sensor in a feedback loop.

Optionally, the method additionally comprises: controlling the secondary light source to emit light at an intensity based on processing results from previously captured image from the image sensor in feedback loop.

Unless otherwise defined herein, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Additional objects and features of the present invention will become apparent upon reading of the detailed description of the invention and the appended claims provided below, and upon reference to the drawings in which:

DETAILED DESCRIPTION OF THE INVENTION

It is understood that the below described and depicted particular cases of embodiments of the invention are presented for illustration and not to limit the invention to such examples. Those skilled in the art will find or will be able to provide, based on routine experimenting, one or more equivalents of the embodiments of the invention disclosed herein. Such equivalents shall be included into the scope of the following claims.

Embodiments of the present invention are directed to methods and systems for yarn quality monitoring, for example, for yarns used in the textile industry.

Figure 1:
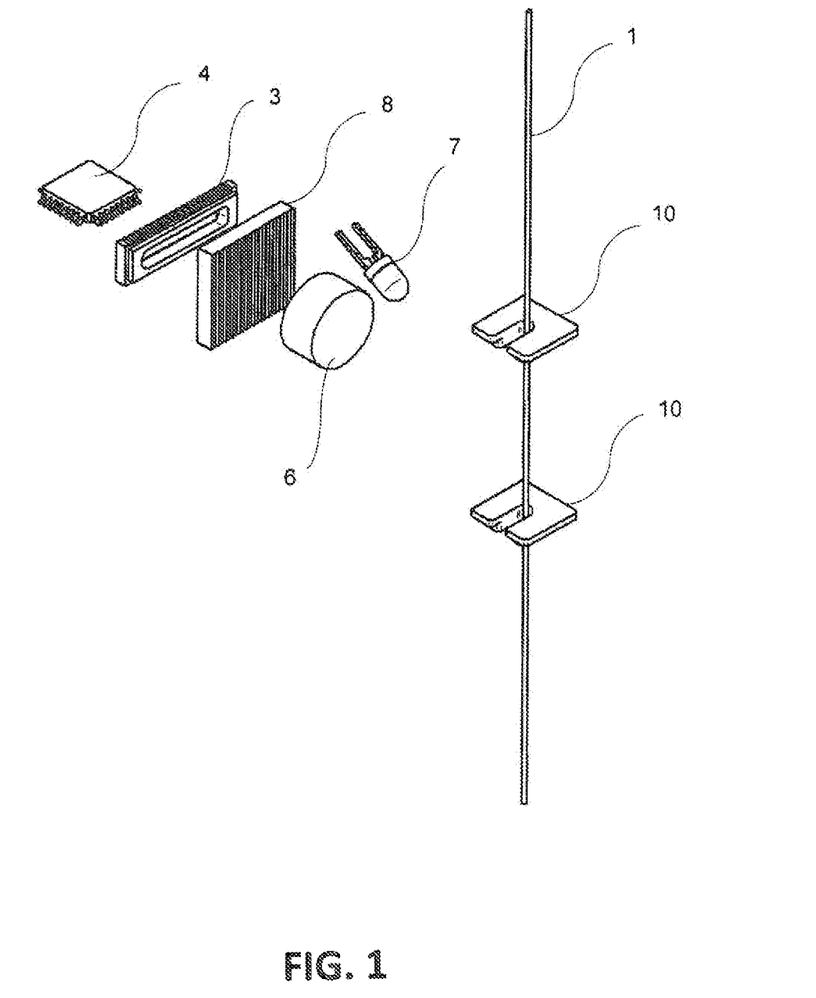
FIG. 1 is a perspective view of a system in accordance with an embodiment of the invention.

FIG. 1 shows a yarn quality monitoring system in an exemplary system in accordance with the present invention, for measuring the presence of foreign fibers and diameter of the yarn 1. The yarn 1 is moved, for example, vertically, and stabilized for measurement by guiding elements 10.

A primary artificial light source 7, also known as a primary light source, is placed on the side of the yarn 1, which also includes the image sensor 3. The primary light source 7 illuminates the yarn 1. Additional primary light sources, similar in position, may be used for detecting of various foreign fibers or to increase illumination intensity. A focusing element 6 and a diffraction element 8 are aligned along an optical path for the light reflected off of the yarn 1, and directed through the focusing element 6, the diffracting element 8, and onto the image sensor 3.

The focusing element 6 renders the device highly immune to dust particles, which accumulate on both optical surfaces (emitter 7 and receiver 3). The focusing element 6 also serves to direct unwanted ambient light rays coming from the sides of the yarn 1, away from the image sensor 3.

The image sensor 3, for example, is formed by at least one line or array of light-sensitive pixels. The pixels are, for example, a square or rectangular shaped light sensitive areas.

Individual pixels may be, for example, monochromatic or sensitive for specific light wavelength ranges. Also, individual pixels or regions of pixels can be covered with an optical filter layer for specific ranges of light wavelengths. This simplifies further processing of the captured images.

Alternately, the image sensor 3 is such that the pixels can include micro lenses for increased sensitivity and limiting of wide angle light rays, such that the image is made sharper. Alternately, the image sensor 3 is a charge coupled device (CCD) type. CCD image sensors are used, as they have high sensitivity and are low cost. In other embodiments, the image sensor 3 is a CMOS type. CMOS image sensors have high speed and low power consumption.

The focusing element 6 is, for example, formed by at least one lens or a combination of lenses, from the group of aspherical lens, mirror lens, convex lens, and concave lens. Lenses or combinations of lenses can be mounted in an M12×0.5 package. The size and pitch of the M12×0.5 package allows for the adjustment of a focus distance, and the M12×0.5 package is available at low costs.

The diffraction element 8 diffracts a portion of the primary artificial light rays reflected from the yarn 1, resulting in the creation of an interference pattern on the image sensor 3. For example, when the primary light source 7 emits white light, a rainbow spectra is created. The remaining part of the reflected light rays pass through the diffraction element 8 undiffracted, and creates a focused yarn image on the image sensor 3. A standard diffraction grating may be used as the diffraction element 8.

This focused yarn image on the image sensor 3, based on light from only the primary light source 7, is processed by the control unit (controller) 4, to provide yarn 1 diameter measurements. The controller 4 is in communication with the image sensor 3.

As the diffraction element 8 is used, a color image sensor, as the image sensor 3, is not necessary, and a monochromatic image sensor may be used as the image sensor 3. Measured yarn segment color information is obtained by processing of light intensity at corresponding pixel positions on the image sensor 3. The monochromatic image sensor, when used as the image sensor, provides for high sensitivity, and high resolution, and is cost effective.

Embodiments of the invention which employ a diffraction element 8 with a zero order mode feature, are such that a portion of the light rays pass undiffracted through the diffraction element 8 and are focused on the image sensor 3 as a yarn image. The interference pattern created by diffracted rays is captured, typically simultaneously, with an image of the yarn 1 by the image sensor 3, and processed for obtaining color analysis and yarn diameter, respectively, by the controller 4. For yarn quality monitoring, yarn 1 color analysis and yarn diameter are typically evaluated from the same yarn segment (from same captured image sensor 3 data).

Additionally, processing of the interference pattern on the image sensor 3 by the controller 4 determines foreign fiber presence in the yarn 1.

The yarn 1 image and its interference pattern are captured by image sensor 3, for example, at the same time. Processing the light intensity of an interference pattern at specific distances from yarn 1 image position on the image sensor 3 is used for color analysis of the yarn 1, which when processed in the controller 4, results in a determination of foreign fiber presence in the yarn 1. Alternately, when detecting of the presence of foreign fibres in the yarn 1, a color image sensor is not necessary. Rather, only a monochromatic image sensor 3 is needed. The primary artificial light source 7 emits light rays at specific wavelengths, including, monochromatic light, RGB light, white light, UV light, IR light, or combinations thereof, for detecting various foreign fiber materials present in the yarn 1.

Figure 2:
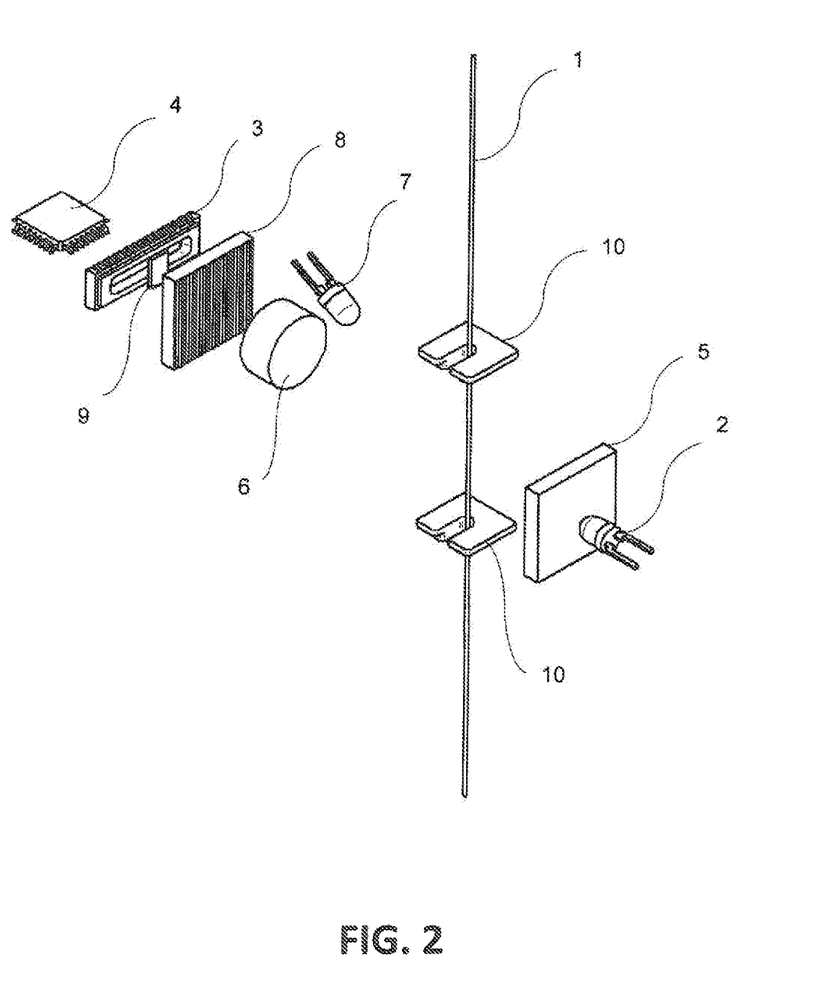
FIG. 2 is a perspective view of a system in accordance with an embodiment of the invention.

Another embodiment of the invention is shown in FIG. 2. In this embodiment of FIG. 2, similar components of the system and device have the same numbers and are in accordance with their descriptions for the system and device of FIG. 1 above, except where specifically indicated.

The system and device of FIG. 2, includes a secondary artificial light source or secondary light source 2 which, for example, has a light wavelength different than that of the primary artificial light source 7. Light from the secondary artificial light source 2 is diffused by a diffuser 5, which is placed between the secondary light source 2 and the yarn 1.

The diffused light directly illuminates the image sensor 3. The longitudinally moving yarn 1 creates an obstacle for diffused light rays illuminating the image sensor 3.

A focusing element 6, in the optical path of the secondary light source 7, directs non blocked light rays through a diffraction element 8. The diffraction element produces a yarn contour image on the image sensor 3. Undiffracted and unblocked light rays, originating from the secondary light source 2 create a yarn contour image on the image sensor 3. The "yarn contour image" or "contour image" is created from yarn shadows and nonblocked secondary light source 2 rays.

An optical filter 9, partially covers the image sensor 3, in order to allow only secondary artificial light source 2 rays pass through to the image sensor 3. These secondary light source 2 rays are, for example, used for yarn 1 diameter measurement, while the optical filter 9 blocks light from primary artificial light source 7. The image sensor 3 generates image data for yarn diameter and foreign fiber processing in the control unit 4, as detailed below.

Figure 3:
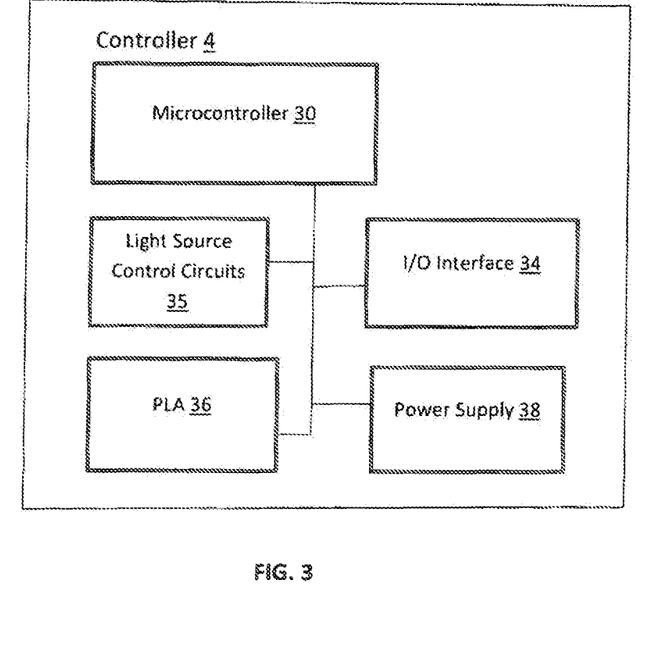
FIG. 3 is a block diagram of the controller of FIGS. 1 and 2.

FIG. 3 shows the control unit or controller 4. The controller 4 includes a computer, such as a microcontroller 30, for example, an integrated circuit having a processor core with other embeded functions, such as I/O (input/output) peripherals, data memory, program memory, and the like. The controller 4 also includes an I/O (input/output) interface 34, light source control circuits 35 and a programmable logic array (PLA) module 36. The PLA 36 module functions in yarn diameter calculations and color analysis from captured image data—yarn images or yarn contour images for diameter calculations and interference pattern for color analysis. The program memory of the microcontroller 30 (e.g., ARM, Atmel AVR, Intel 8051, as well as any combinations thereof) stores executable instructions running the algorithms for determining foreign fiber detection (FIG. 4A), from the color analysis, and yarn evenness (thick and thin places) from yarn diameters (FIG. 4B). The I/O interface module 34 serves for data exchange with a host system. The host system is, for example, a central unit of a spinning machine yarn quality control system (or the central unit of a winding machine yarn quality control system). The host system can be integrated with the central unit of the entire spinning/winding machine, or it can be separate. The host system links to the controller 4 via a communication bus.

The controller 4 also includes light source control circuits 35, which are controlled by the PLA 36. The control unit 4 further includes components, such as a power supply 38, and other known in the art components for controller 4 operation. For example, the image sensor 3 and functionalities of the control unit 4 can be integrated in an Application Specific Integrated Circuit (ASIC circuit), to integrate the image sensor 3 and data processors, e.g., the microprocessor 30 and PLA 36, on a single chip. This simplifies the controller 4 and provides a low cost solution to yarn quality measurement. All of the components of the controller 4 communicate with each other, directly or indirectly.

The controller 4 is such that the parameters of the primary artificial light source 7 and/or the secondary artificial light source 2 are controlled via feedback to the PLA 36. The feedback is based on the quality of previously captured images from the image sensor 3, as linked to the PLA 36. For example, light intensity is increased (as signalled to the primary 7 and secondary 2 light sources from the light source control circuits module 35), when images with low light intensity were previously captured by the image sensor 3.

Figure 4A:
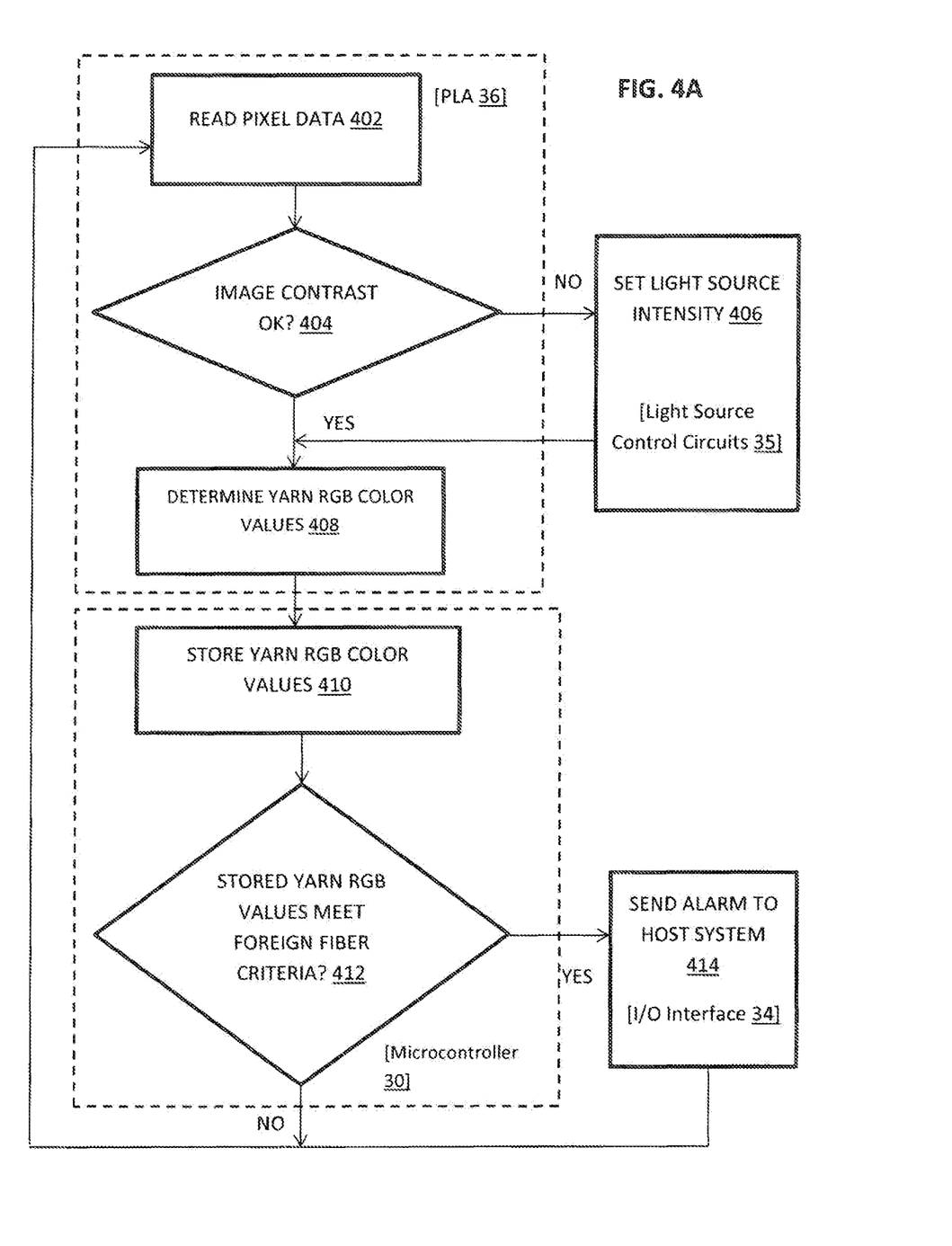
FIGS. 4A and 4B are flow diagrams of processes performed by the systems of FIGS. 1 and 2, for determining foreign fiber presence and yarn diameter.
Figure 4B:
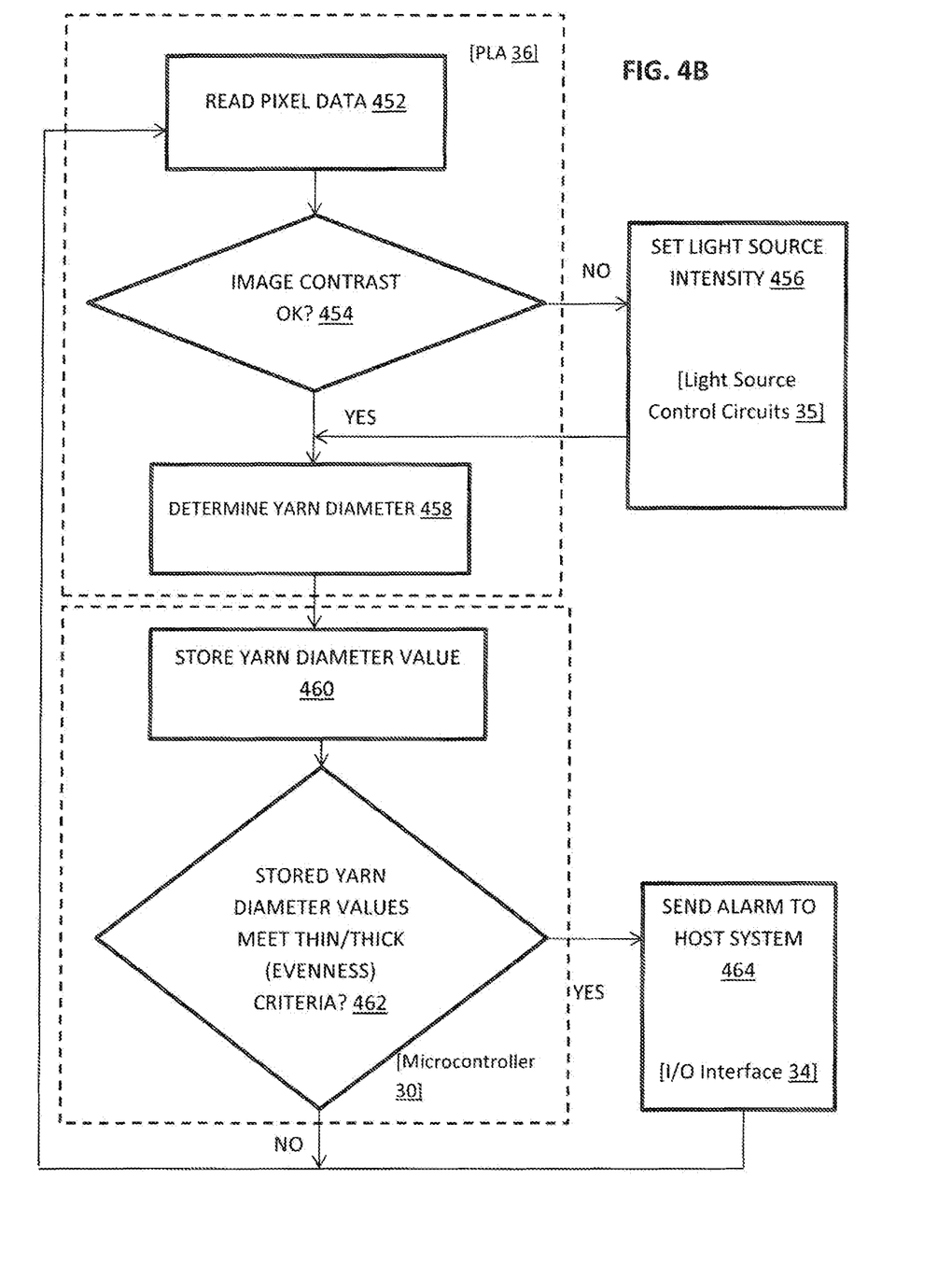

Attention is now directed to FIGS. 4A and 4B, which show flow diagrams detailing computer-implemented processes in accordance with embodiments of the disclosed subject matter. Reference is also made to elements shown in FIGS. 1-3. The process and subprocesses of FIGS. 4A and 4B are computerized processes performed by the controller 4. The aforementioned processes and sub-processes can be, for example, performed manually, automatically, or a combination thereof, and, for example, in real time.

In FIG. 4A yarn foreign fiber analysis and determination begins as pixel data, based on primary light source 7 light reflected from the yarn 1, is read by the PLA 36, at block 402, for each yarn segment of a predetermined length. The PLA 36 then applies rules and policies to the read pixel data, to determine whether the image contrast is within a predetermined range, at block 404.

If no at block 404, the process moves to block 406, where the light source intensity, for example, of the primary light source 7, is set to result in acceptable image contrast in the next measuring cycle, by the light source control circuits 35, at block 406. From block 406, the process moves to block 408. Also, at block 404, should the image contrast be within a predetermined range, the process also moves to block 408. At block 408, the PLA 36 determines RGB (Red-Green-Blue) color values (so called color analysis) for the yarn segment, for example, by processing light intensities of image sensor 3 pixels at specific positions relative to the position of the yarn image.

From block 408, the process moves to block 410, where each determined RGB color value is stored in data memory associated with the microcontroller 30. It is then determined by the microcontroller 30, whether the history of stored yarn RGB color values (currently and previously stored values) meet a predetermined criteria for foreign fibers, at block 412. If yes, there were sufficient foreign fibers in the yarn for several consecutive measured yarn segments to cause the I/O Interface 34 to send a foreign fiber alarm to the host system, at block 414. From block 414, or if no, at block 412, the process returns to block 402, from where it continues.

In FIG. 4B, yarn diameter analysis and determination begins as pixel data (from the image sensor 3), based on light emitted from the secondary light source 2, is read by the PLA 36, at block 452, for each yarn segment of a predetermined length. The PLA 36 then applies rules and policies to the read pixel data, to determine whether the image contrast is within a predetermined range, at block 454.

If no at block 454, the process moves to block 456, where the light source intensity, for example, of the secondary light source 2, is set to obtain an acceptable image contrast in the next measuring cycle, at block 456. From block 456, the process moves to block 458. Also, at block 454, should the image contrast be within a predetermined range, the process also moves to block 458. At block 458, the PLA 36 determines the yarn diameter, by processing the data from the pixels by, for example, a threshold method (binarizing the pixels data and counting pixels which corresponds to the yarn).

From block 458, the process moves to block 460, where each determined yarn diameter value for each captured yarn segment image is stored in the microcontroller 30. It is then determined by the microcontroller 30, at block 462, whether the history of stored yarn diameter values fail to meet a predetermined criteria for thickness. If yes, the yarn diameter is outside of an acceptable range for several consecutive measured yarn segments (for any number of predetermined segments designating a sample size of the like), e.g., yarn evenness being too thin or too thick, and the I/O Interface 34 sends a yarn eveness alarm to the host system, at block 464. From block 464, or if no, at block 462, the process returns to block 452, from where it continues.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

The above-described processes including portions thereof can be performed by software, hardware and combinations thereof. These processes and portions thereof can be performed by computers, computer-type devices, workstations, processors, micro-processors, other electronic searching tools and memory and other non-transitory storage-type devices associated therewith. The processes and portions thereof can also be embodied in programmable non-transitory storage media, for example, compact discs (CDs) or other discs including magnetic, optical, etc., readable by a machine or the like, or other computer usable storage media, including magnetic, optical, or semiconductor storage, or other source of electronic signals.

The processes (methods) and systems, including components thereof, herein have been described with exemplary reference to specific hardware and software. The processes (methods) have been described as exemplary, whereby specific steps and their order can be omitted and/or changed by persons of ordinary skill in the art to reduce these embodiments to practice without undue experimentation. The processes (methods) and systems have been described in a manner sufficient to enable persons of ordinary skill in the art to readily adapt other hardware and software as may be needed to reduce any of the embodiments to practice without undue experimentation and using conventional techniques.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:
1. A yarn quality monitoring device, comprising:
a primary light source for illuminating the yarn;
an image sensor illuminated by light from primary light source light reflected from the yarn and propagating along an optical path to the image sensor, the image sensor for capturing an image data;

a focusing element in the optical path between yarn and image sensor, for focusing the reflected light on the image sensor;

a diffraction element in the optical path between yarn and image sensor, for diffraction of primary light source light reflected from the yarn;

a controller for processing the image data to obtain color analysis of yarn and yarn diameter;

a secondary light source emitting light, the light propagation defining an optical path; and a diffuser proximate to the secondary light source for diffusing the emitted light, the diffused light illuminates the image sensor over the optical path through the focusing element and the diffraction element, such that yarn placed as an obstacle in the optical path creates a yarn contour image on the image sensor used by the controller for yarn diameter processing;

wherein the primary light source and the secondary light source emit light at different wavelengths, and the device further includes an optical filter at least partially covering the image sensor for blocking light reflected from the yarn illuminated by the primary light source.

2. The device of claim 1, wherein the diffraction element is a diffraction grating.

3. The device of claim 2, wherein the primary light source emits one or more light types including monochromatic light, Red-Green-Blue (RGB) light, white light, ultraviolet light (UV) or infrared (IR) light.

4. The device of claim 1, wherein the focusing element includes one or more lenses selected from the group consisting of aspherical lenses, mirror lenses, convex lenses, concave lenses and combinations thereof.

5. The device of claim 1, wherein the focusing element includes one or more lenses in an M 12×0.5 package.

6. The device of claim 1, wherein the image sensor comprises: one or more lines of photosensitive pixels; and the image sensor is a type of a complementary metal oxide semiconductor (CMOS) sensor or a charge coupled device (CCD).

7. The device of claim 1, wherein the image sensor includes micro lenses, configured to limit wide angle light rays.

8. The device of claim 1, wherein the controller comprises:

a programmable logic array (PLA) for image data processing, to obtain yarn diameter and/or yarn color analysis;

a light control circuit in communication with the PLA, which is controlled by the PLA; and a microcontroller in communication with the PLA, the microcontroller programmed to evaluate the yarn evenness, and/or the yarn foreign fiber content, from the processed image data.

\* \* \* \* \*